US010383638B2

(12) United States Patent
Cheal et al.

(10) Patent No.: US 10,383,638 B2
(45) Date of Patent: *Aug. 20, 2019

(54) SYSTEM AND METHOD FOR BONE PREPARATION FOR AN IMPLANT

(71) Applicant: OMNIlife science, Inc., Raynham, MA (US)

(72) Inventors: Edward J Cheal, Duxbury, MA (US); George Cipolletti, Duxbury, MA (US); David L Lasalle, Wrentham, MA (US); Carl Knobloch, Duxbury, MA (US); Christopher Plaskos, Plymouth, MA (US)

(73) Assignee: OMNIlife science, Inc., Raynham, MA (US)

( * ) Notice: Subject to any disclaimer, the term of this patent is extended or adjusted under 35 U.S.C. 154(b) by 297 days.

This patent is subject to a terminal disclaimer.

(21) Appl. No.: 15/347,188

(22) Filed: Nov. 9, 2016

(65) Prior Publication Data

US 2017/0056022 A1    Mar. 2, 2017

Related U.S. Application Data

(63) Continuation of application No. 14/982,784, filed on Dec. 29, 2015, now abandoned, which is a continuation of application No. 13/524,424, filed on Jun. 15, 2012, now Pat. No. 9,220,510.

(60) Provisional application No. 61/497,326, filed on Jun. 15, 2011.

(51) Int. Cl.
*A61B 17/15* (2006.01)
*A61B 34/10* (2016.01)
*A61B 90/00* (2016.01)
*A61B 17/17* (2006.01)
*A61F 2/46* (2006.01)
*A61B 34/30* (2016.01)

(52) U.S. Cl.
CPC ............ *A61B 17/155* (2013.01); *A61B 17/17* (2013.01); *A61B 34/10* (2016.02); *A61B 90/37* (2016.02); *A61F 2/46* (2013.01); *A61F 2/4657* (2013.01); *A61B 34/30* (2016.02); *A61B 2034/105* (2016.02); *A61B 2034/107* (2016.02); *A61F 2002/4633* (2013.01)

(58) Field of Classification Search
CPC ........................ A61B 17/1764; A61B 19/2203
See application file for complete search history.

(56) References Cited

U.S. PATENT DOCUMENTS

2011/0087332 A1* 4/2011 Bojarski .............. A61B 17/155
623/20.32

* cited by examiner

*Primary Examiner* — Andrew Yang
(74) *Attorney, Agent, or Firm* — Kim IP Law Group PLLC

(57) ABSTRACT

A computer assisted surgical system for guiding bone cutting operations of an arthroplasty surgery is provided. The computer assisted surgical system includes a cutting guide having a guiding surface for mounting to a bone and a computer. The computer is in communication with the cutting guide and configured to generate a bone model of the first bone without the use of pre-operative bone images, determine a position of an implant model having a bone interface surface on the bone model, determine a position of the cutting guide on the first bone based on the determined position of the implant model on the bone model, and position the guiding surface of the cutting guide to one of a plurality of predetermined cut configurations relative to the bone interface surface.

21 Claims, 4 Drawing Sheets

SYSTEM AND METHOD FOR BONE PREPARATION FOR AN IMPLANT

CROSS-REFERENCE TO RELATED APPLICATIONS

This application is a continuation of U.S. patent application Ser. No. 14/982,784 filed on Dec. 29, 2015, which is a continuation of U.S. patent application Ser. No. 13/524,424 filed on Jun. 15, 2012, which claims the benefit of U.S. Patent Application No. 61/497,326 filed Jun. 15, 2011, the entire disclosures of which are hereby incorporated by reference in their entirety.

BACKGROUND OF THE INVENTION

The present invention relates to an improved system and method for bone preparation for an implant. In particular, the present invention relates to a computer assisted surgical system and method for resecting bone to receive an orthopedic implant for press-fit applications.

Arthroplasty or joint replacement surgical procedures require accurate bone preparation for the implantation of prosthetic components i.e., implants. A precise fit between the implant and resected bone is desired for good fixation in both cementless and cemented applications in order to prevent loosening of the implant over time. Furthermore, an interference fit or "press-fit" is often desired to ensure good fixation of the implant to the bone, and for osteointegration of cementless devices. The amount of interference fit to apply, however, is difficult to ascertain and often determined by empirical methods with the benefit of intra-operative evaluations of the patient's bone.

For example, in a total knee joint replacement surgery, the distal femur, proximal tibia and patellar articulating surfaces are replaced with prosthetic components. The femoral component typically requires that the distal femur be resected with e.g., five bone cuts that are made at angles to one another when viewed from a sagittal perspective. The bone cuts are commonly performed with a bone cutting tool, such as a saw or a mill that is guided by a manual cutting block or a template.

Surgical cutting blocks can have integrated cutting slots or open surfaces that correspond to the inner shape of the implant to be used. These guiding surfaces are at fixed distances and angles from one another so that one cutting block must be provided for each size and shape of the implant or a limited range of sizes of the type of implant.

Implants used in cementless applications often incorporate a porous coating about its bone interface surface. The porous coating is typically structured so as to be dimensionally offset from the implant's bone interface surface. That is, the porous coating typically sits proud of the implant's bone interface surface. However, regardless of whether or not an implant is to be used for cemented or cementless applications, the bone preparation i.e., bone cuts are typically the same. That is, the same cutting blocks/jigs are used to guide the bone cuts for implants used for either cementless or cemented applications. Therefore, the resulting discrepancy between the bone cut formed using the cutting block and the internal bone interface surface of the implant (which may be at least in part determined by the thickness of the coating) provides a nominal degree of press-fit interference between the bone cuts as established by the cutting block and the implant once it is impacted onto the resected bone. Alternatively, a manual cutting block can be used with cutting planes that are slightly offset and/or angled from the inner surfaces of the implant to achieve a predetermined and fixed amount of interference.

One of the challenges orthopaedic surgeons face in the operating room is the varying quality of bone they are presented with at surgery. Patients undergoing joint replacement surgery typically suffer from degenerative conditions that can alter bone quality. Thus, from one patient to another, the surgeon may encounter varying degrees of bone quality. For example, upon exposing the patient's joint and bones, the surgeon may encounter bone that is very poor in quality, having a relatively low density or high porosity. On other occasions, for example, in younger more active patients, the bone can be relatively dense and hard. The quality of bone can affect the degree or tightness of the fit of the implant for a given amount of interference. Hence, when bone cuts are prepared in the same fashion for all patients, the resulting tightness or degree of the fit can vary from one patient to another depending upon the bone quality, which may ultimately impact the overall short term and long term success of the implant. However, there are currently no tools available that allows the surgeon to precisely and objectively adjust the bone cuts during a surgical procedure in order to customize the degree of press-fit interference between the implant and resected bone for individual patients that takes into account the varying quality of bone of individual patients.

Another disadvantage of conventional systems used in arthroplasty is that they lack flexibility in the ability to adjust the relative positions of the bone cuts for any particular implant, which can allow for varying the resulting degree of interference press-fit achieved between the resected bone and the implant being used. Additionally, conventional systems cannot provide multiple levels of interference press-fit in an all-in-one device. For example, in a manual set of instruments, once the cutting blocks are manufactured they cannot be changed and the surgeon needs to accept those relative cut locations for all patients and surgical circumstances.

Therefore, a need still exists for a system and method for the preparation of bone to receive an implant that can provide intra-operative flexibility to a surgeon user and allow for variations in the degree of press-fit interference provided based upon pre or intra-operative assessment of the patient e.g., bone quality and implant trialing. Such a need is met by the system and method of the present invention.

BRIEF SUMMARY OF THE INVENTION

In an embodiment, the present invention provides a computer assisted surgical system for guiding bone cutting operations of an arthroplasty surgery including a cutting guide and a computer. The cutting guide has a guiding surface and mounts to a bone. The computer is in communication with the cutting guide, which can be a robotic cutting guide. The computer is configured to intra-operatively generate a bone model of the bone without the use of pre-operative bone images, determine a position of an implant model having a bone interface surface on the bone model, determine a position of the cutting guide on the bone based on the determined position of the implant model on the bone model, and position the guiding surface of the cutting guide to one of a plurality of predetermined cut configurations relative to the bone interface plane. The bone model can also be generated intra-operatively.

In another embodiment, the present invention provides a method of preparing a first bone for an implant during an arthroplasty. The method includes generating a bone model of the first bone and providing an implant model having a bone interface. An optimum position of the implant model on the bone model is then determined and a quality of the first bone is intra-operatively evaluated. The method further includes selecting a degree of interference fit between the implant model and the bone model based on the intra-operative evaluation of the quality of the first bone and mounting a cutting guide having a cutting guide surface on the first bone based on the determined optimum position. The cutting guide surface is positioned to one of a plurality of predetermined cut configurations that corresponds to the selected degree of interference fit.

In yet another embodiment, the present invention provides a method of preparing a first bone for an implant during an arthroplasty. The method includes providing a computer assisted surgery system configured to generate a bone model of the first bone. The computer assisted surgery system includes a memory having a plurality of implant models and a set of default user preferences for resecting bone based on a selected implant model. The method further includes selecting an implant model and determining an optimum position of the implant model on the bone model and attaching a cutting guide in communication with the computer assisted surgery system to the first bone. Further, the method includes automatically aligning the cutting guide to correspond to the default user preferences for resecting bone based on the selected implant model and intra-operatively evaluating a quality of the first bone. Then it is determined if a repositioning of the cutting guide from the default user preferences is required.

In a further embodiment, the present invention provides a computer assisted surgical system for guiding bone cutting operations of an arthroplasty surgery that includes a cutting guide and a computer. The cutting guide is to be positioned relative to a first bone. The computer has a plurality of predetermined cut configurations that corresponds to various degrees of interference fit of a prosthesis on the first bone and is in communication with the cutting guide. The computer is also configured to position the cutting guide to one of the plurality of predetermined cut configurations.

In yet a further embodiment, the present invention provides a method of preparing a bone for an implant during an arthroplasty. The method includes providing a computer assisted surgery system having a plurality of predetermined cut configurations and selecting a degree of interference fit between an implant and a bone that corresponds to one of the plurality of predetermined cut configurations. A cutting guide is then positioned to one of a plurality of predetermined cut configurations corresponding to the selected degree of interference.

In another embodiment, the present invention provides a method of preparing a first bone for an implant during an arthroplasty. The method includes providing a computer assisted surgery system having a set of default user preferences for resecting bone that corresponds to an interference fit of a prosthesis on the first bone and positioning a cutting guide in communication with the computer assisted surgery system relative to the first bone. The method further includes aligning the cutting guide to correspond to the default user preferences for resecting bone and intra-operatively evaluating a quality of the first bone. Then it is determined if a repositioning of the cutting guide from the default user preferences is required.

In yet another embodiment, the present invention provides a robotic cutting guide for guiding bone cutting operations of an arthroplasty surgery that includes a guiding member and a plurality of predetermined cut configurations that corresponds to various degrees of interference fit of a prosthesis on the bone. The guiding member is positioned relative to a bone. The robotic cutting guide is also configured to intra-operatively receive a first selection of one of the plurality of predetermined cut configurations and move the guiding member to the first selected predetermined cut configuration. The robotic cutting guide can also receive a second selection of one of the plurality of predetermined cut configurations and move the guiding member to the second selected predetermined cut configuration.

In accordance with a first aspect, the present invention also provides a computer assisted surgical system for cutting bone that includes a guide and a navigation system in communication with the guide. The guide guides a cutting tool for cutting bone. The guide is pivotably mountable to bone about a first axis of the guide, and includes a saw guide coupled to a second axis of the guide. The navigation system includes a display and a system controller in communication with the display. The system controller is configured to store in memory dimensional data and standard cutting plane data associated with an implant to be implanted to the bone, receive input for a desired bone resection associated with a desired degree of implant-bone interference for a press-fit application, position the saw guide in alignment with or at an off-set with the standard cutting planes based upon the received input for the desired bone resection, and display image and dimensional data of the implant in combination with the bone based upon the inputted desired bone resection.

In a second aspect, the present invention provides a method of preparing bone for receiving an implant. The method includes the steps of attaching a pivotable guide to a bone, assessing a desired degree of press-fit interference between the implant and the bone, inputting the desired degree of bone resection based upon the assessed desired degree of press-fit interference to a navigation system associated with the pivotable guide and positioning the pivotable guide to a position based upon the inputted desired degree of bone resection. The method can further include the steps of resecting bone with the pivotable guide, assessing an interference fit between the implant and resected bone, inputting another desired degree of bone resection based upon the assessed press-fit interference between the implant and the bone, and repositioning the pivotable guide to a subsequent position based upon the inputted desired degree of bone resection after the assessment of the press-fit interference. Furthermore, the method can include the step of assessing a desired degree of press-fit interference between the implant and the bone based upon bone quality data of the bone.

In a third aspect, the present invention provides a flexible system that gives a surgeon the ability to intra-operatively customize bone cuts according to the surgeon's preference and/or individual patient factors.

A fourth aspect, the present invention provides the ability to intra-operative select the degree of press-fit interference either at the beginning of or during the surgical procedure.

A fifth aspect of the present invention provides the ability to select from a plurality of cut configurations that correspond to varying amounts of congruency or interference between the inner implant surface and outer surface of the resected or cut bone.

A sixth aspect of the present invention provides the ability to modify the degree of press-fit interference or congruency on planar bone cuts (e.g., bone cuts made during a TKA) as well as for curved bone cuts (e.g., during a resurfacing procedure). For example: 0 degrees or 0 mm of press-fit, ¼, ½, ¾, 1, 1¼, etc. degrees or mm can be applied and the ability to vary a continuous parameter that changes the amount of press-fit interference (e.g., X degrees or mm).

A seventh aspect of the present invention provides the ability to assess the quality of the patient's bone and to use this information in a decision making process in order to select the appropriate amount of press-fit interference that is most optimal for a specific patient.

An eighth aspect of the present invention provides the ability to perform one or more resections before deciding which bone cut configuration to use (for example a distal cut, or an anterior cut).

A ninth aspect of the present invention provides the ability to assess the amount of bone coverage between an implant and bone surface in order to determine how much press-fit interference to apply to the patient based on the patient's native morphology and the planned positioning of the femoral implant component.

A tenth aspect of the present invention provides a display of a color map on an implant planning screen (superimposed over the modeled bone cut-surfaces) that is indicative of the intensity of the currently selected interference fit between the resected bone and the implant.

An eleventh aspect of the present invention provides a system for determining an optimal degree of fit between an implant and a resected bone without requiring any preoperative medical images of the bone, such as CT, MRI or X-rays.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings an embodiment which is presently preferred. It should be understood, however, that the invention is not limited to the precise arrangements and instrumentalities shown.

In the drawings.

DETAILED DESCRIPTION OF THE INVENTION

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Unless specifically set forth herein, the terms "a," "an" and "the" are not limited to one element but instead should be read as meaning "at least one." The term "distal" means situated away from the point of origin or attachment and the term "proximal" means situated toward the point of origin or attachment. The terminology includes the words noted above, derivatives thereof and words of similar import.

Figure 1:
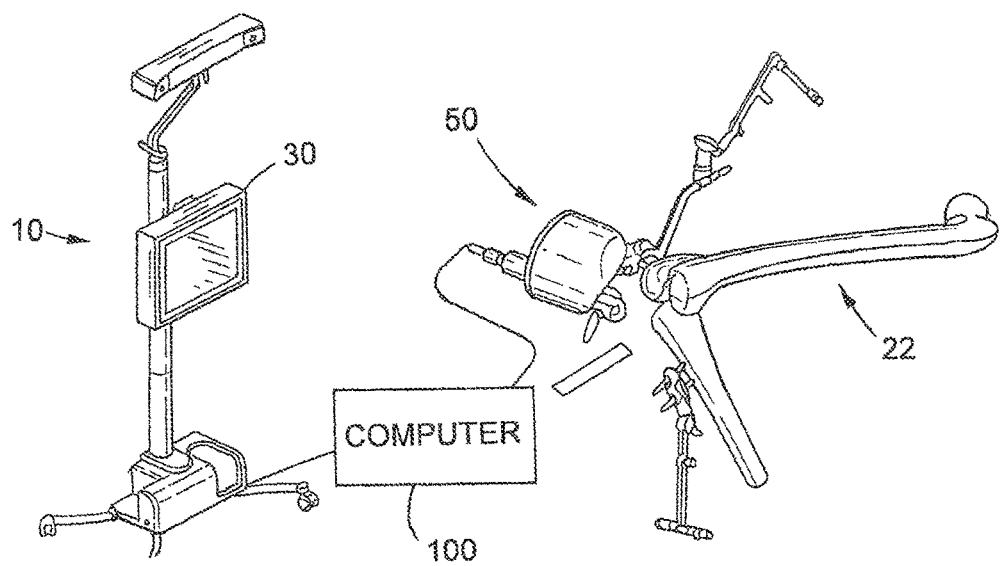
FIG. 1 is a perspective view of a computer assisted surgical system in accordance with a preferred embodiment of the present invention.

In a first preferred embodiment, the present invention provides a computer assisted surgical system (CAS) 10 (FIG. 1) for guiding bone cutting operations of an arthroplasty surgery. The CAS 10 includes a robotic guide positioning device (also referred to as a robotic cutting guide, a robotic guide, or cutting guide) 50 for guiding a cutting tool for cutting bone. The cutting guide 50 is preferably in communication with and operably connected to the CAS 10, e.g., in communication with a computer 100 of the CAS 10. That is, the cutting guide 50 can be wired to the computer 100 or remotely controllable by the computer 100 to move and guide the cutting guide 50. Exemplary examples of total knee replacement manual and robotic bone-cutting guides applicable to the present invention are disclosed in U.S. Pat. Nos. 5,817,097; 4,574,794; 5,571,110 and 6,554,837, and U.S. Patent Application Publication Nos. 2010/0130986, 2011/0130761, and 2006/0200161, the disclosures of which are hereby incorporated by reference herein in their entirety. Exemplary examples of computer assisted surgical systems or navigation systems are disclosed in U.S. Patent Application Publication Nos. 2007/0185498, 2007/0106128, 2006/0161052, 2009/0018445, 2011/0069867 and 2004/0127788 and U.S. Pat. Nos. 6,738,656; 6,527,443; 6,226,548 and 5,682,886, and International Application Publication Nos. WO2006/106419 and WO99/60939, the entire disclosures of which are hereby incorporated by reference herein in their entirety.

The present invention is applicable to any arthroplasty surgery. However, for exemplary purposes only, the present invention will hereinafter be described with reference to a total knee arthroplasty surgery.

Figure 6:
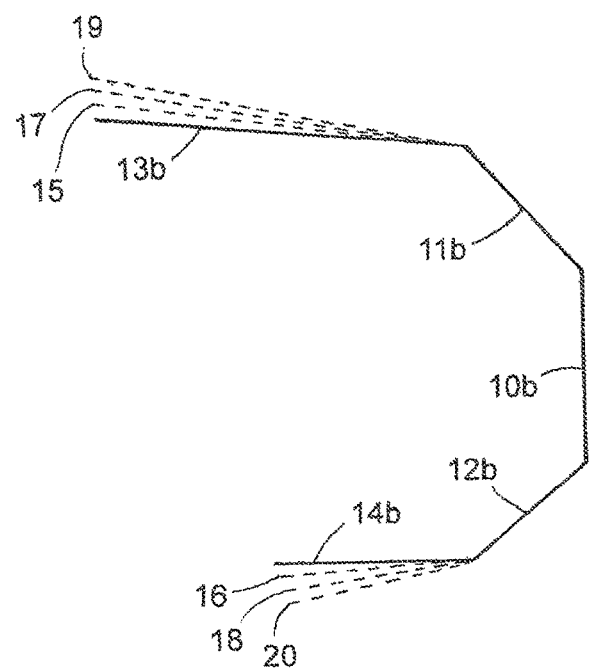
FIG. 6 is a sagittal view of an exemplary set of bone cuts to a distal femur made with the robotic guide of FIG. 2 in accordance with a method of the present invention.
Figure 3:
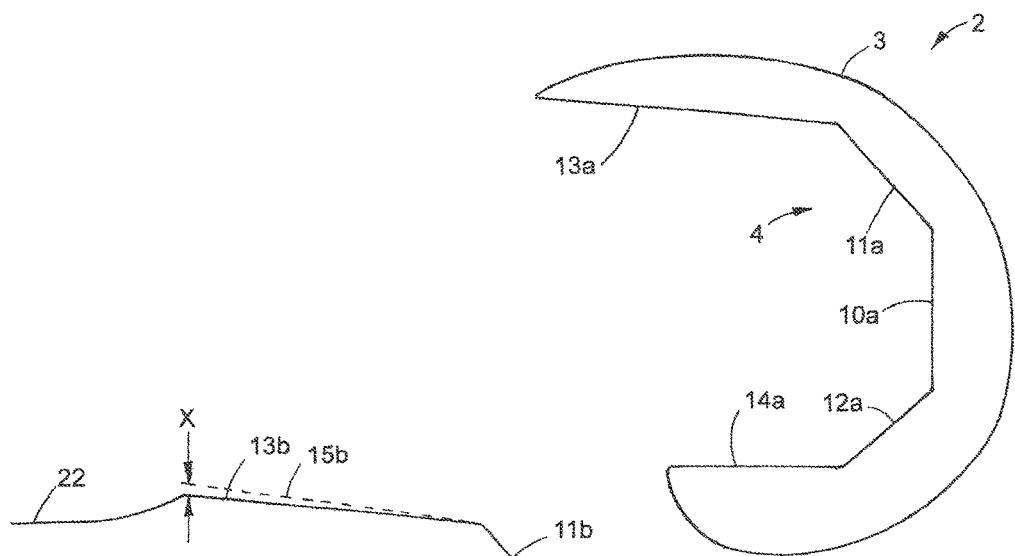
FIG. 3 is a sagittal view of a conventional femoral implant.
Figure 4:
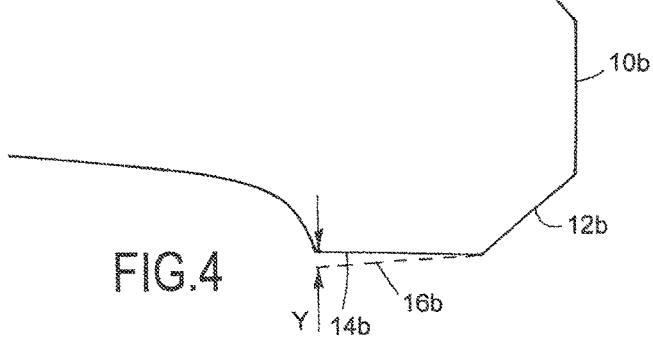
FIG. 4 is a sagittal view of a resected distal femur bone for receiving the femoral implant of FIG. 3.
Figure 5:
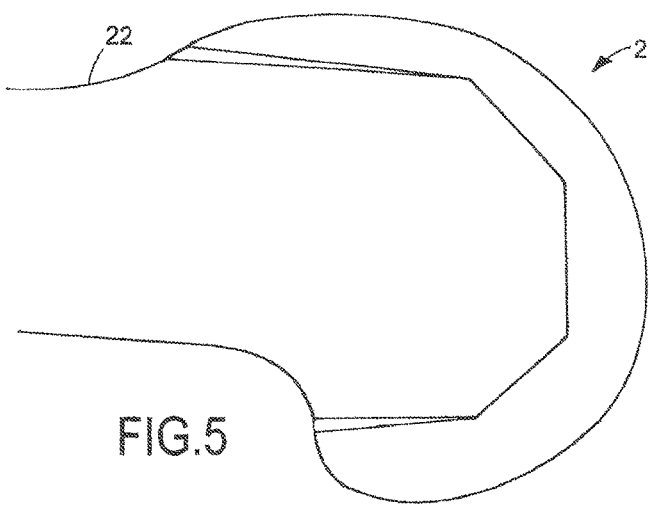
FIG. 5 is a sagittal view of the distal femur bone of FIG. 4 assembled to the femoral implant of FIG. 3.

FIG. 3 illustrates a side (sagittal) view of a conventional femoral prosthesis/implant 2 applicable to a total knee arthroplasty. The femoral prosthesis 2 includes internal or inner surfaces 4 that are intended to directly engage or be fixed to a distal aspect of a resected distal femur bone 1, as shown in FIGS. 4 and 5. The inner surfaces 4 are made up of a plurality of planar cuts, in this case five planar surfaces, including a distal cut surface 10*a*, an anterior chamfer cut surface 11*a*, an anterior cut surface 13*a*, a posterior chamfer cut surface 12*a*, and a posterior cut surface 14*a*. Referring to FIG. 6, in order to fit the femoral prosthesis 2 onto the resected distal femur bone 1, the femoral bone is prepared with a series of planar cuts that correspond to the inner surfaces 4 of the femoral prosthesis 2, namely a distal cut 10*b*, anterior chamfer cut 11*b*, anterior cut 13*b*, posterior chamfer cut 12*b*, and posterior cut 14*b* (FIG. 6). In this case, the distal femoral bone cuts 10*b*, 11*b*, 12*b*, 13*b*, 14*b* are standard cuts that are congruent or co-planar with the internal bone interface planes/surfaces of the femoral prosthesis 2 (i.e., surfaces 10a, 11a, 12a, 13a, 14a). The femoral prosthesis 2 also contains an outer surface 3 that is intended to articulate with a tibial component (not shown) and an optional patellar component (not shown).

Figure 2:
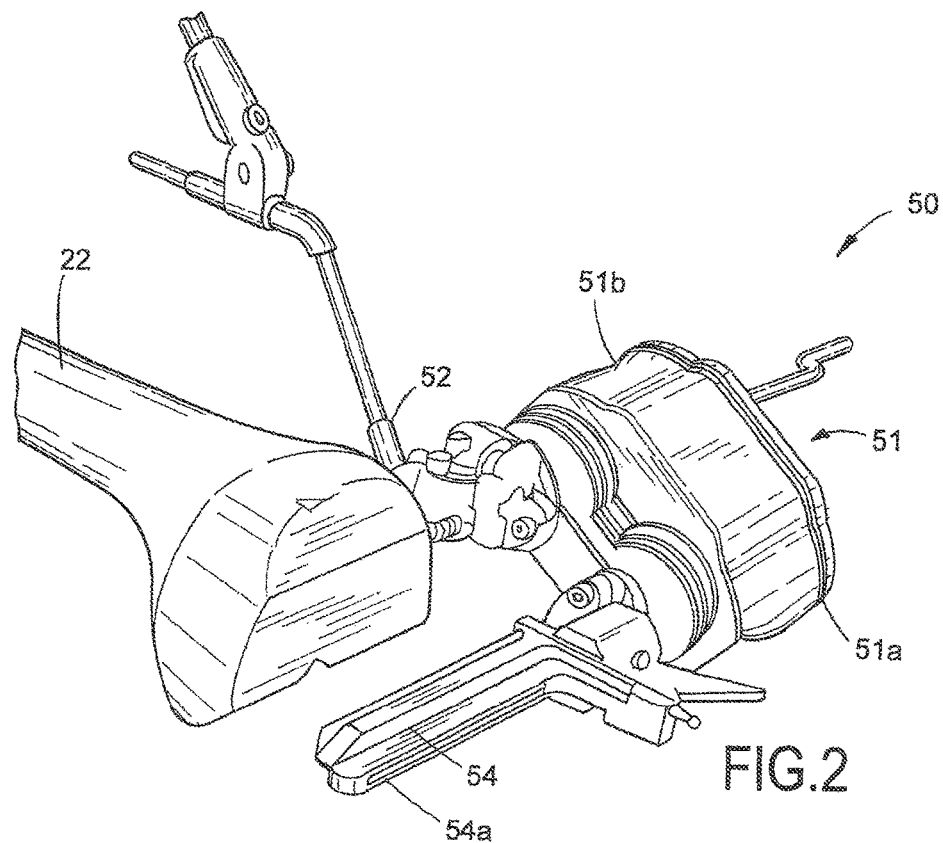
FIG. 2 is a perspective view of a robotic guide applicable to a total knee arthroplasty in accordance with a preferred embodiment of the computer assisted surgical system of FIG. 1.

Referring back to FIGS. 1 and 2, the robotic guide 50 has a guiding surface or guiding member for mounting to or positioning relative to a bone for use in e.g., a total knee arthroplasty is shown. The robotic guide 50 is disclosed for use in a total knee arthroplasty for exemplary purposes only and can alternatively be configured as a robotic guide positioning device for any other joint replacement procedure.

The robotic guide 50 is a bone-mountable robotic guide 50 that includes a motor unit 51 having two axes of rotation 51a and 51b. The first axis 51b is coupled to a bone 22 via a bone fixation base 52, and the second axis 51a is coupled to a saw-guide 54. The saw-guide 54 includes a slot (also referred to as a guiding surface) 54a for guiding a cutting tool, such as an oscillating saw-blade (not shown). The robotic guide 50 is capable of positioning the saw-guide 54 at any angle and resection depth such that it can be aligned with any of the femoral bone cuts 10b, 11b, 12b, 13b, 14b.

In other words, the robotic guide 50 is e.g., a cutting guide for guiding a cutting tool capable of cutting bone portions at the level of a head of a femoral bone that includes a seat 52 configured to fasten to a side of the femoral bone adjacent to distal condyles where the femoral bone is to be cut. The seat 52 is coupled to the femoral bone about a first rotation axis. The robotic guide 50 also includes a means for adjusting in two substantially perpendicular directions the first rotation axis with respect to the seat including after the robotic guide 50 is fastened to the femoral bone. The robotic guide 50 also includes first and second motors 51 and an arm supporting the first and second motors 51 that are spaced a fixed distance from one another in all operating positions of the robotic guide, with one end of the arm being pivotally assembled on the seat 52 according to the first rotation axis. The robotic guide 50 further includes a cutting guide surface 54a configured to guide the cutting tool and is pivotally assembled on the arm according to a second rotation axis where the second motor is operatively coupled to the cutting guide surface 54a for rotating the cutting guide surface 54a about the second rotation axis, where a distance between the first and second rotational axes is also fixed in all operating positions of the device.

The robotic guide 50 is described in more detail in U.S. Patent Application Publication Nos. 2011/0130761 entitled "Robotic guide assembly for use in computer-aided surgery," and 2010/0130986 entitled "Surgical robotic system," and U.S. Pat. No. 8,096,997 entitled "Guiding Device for Bone Cutting," the entire disclosures of which are hereby incorporated by reference herein in their entirety.

The robotic guide 50 is a component of the computer assisted surgical system or CAS 10, which can include several additional components. Such additional components can include a 3D localizer for measuring or "tracking" the position of tools in 3D space, and software that has the capability to register patient data, plan the position and size of implant, control guide positioning through motion and robot controllers, and check cut surfaces, and so forth. Exemplary computer assisted surgical systems applicable to the present invention are described in more detail in U.S. Patent Application Publication Nos. 2007/0106128 entitled "Computer assisted surgery system" and 2007/0185498 entitled "System for determining the position of a knee prosthesis," the entire disclosures of which are hereby incorporated by reference herein in their entirety.

In accordance with the present example, the CAS 10 is configured to generate a bone model of a first bone having a bone interface surface, e.g., a femoral bone 22, without the use of preoperative bone images. Such a bone model can be generated by a computer 100 of the CAS 10 configured to deform a generic model of a bone in response to a plurality of positions of a tracking device that are specific to a patient. A detailed discussion of such means to generate a deformed bone model is disclosed in U.S. Pat. No. 8,126,533, the entire disclosure of which is hereby incorporated by reference herein in its entirety.

The computer 100 of the CAS 10 is further configured to determine a position of the implant model of the femoral prosthesis 2 on the bone model. Preferably, the computer 100 determines an optimal position of the implant model on the bone model. Further details of such means to determine an optimal position of the implant model on the bone model is disclosed in U.S. Pat. No. 8,126,533, the entire disclosure of which is hereby incorporated by reference herein in its entirety. The computer 100 is further configured to display planned resection contours corresponding to one of a plurality of predetermined cut configurations on the display, as further discussed below.

The CAS 10 is also configured to determine a position of the robotic guide (i.e., cutting guide) 50 on the bone 22 based on the determined position of the implant model on the bone model by the computer of the CAS 10. The robotic guide 50 further aligned or positioned with the standard cutting planes of the prosthesis (i.e., 10a, 11a, 12a, 13a, 14a). In the present embodiment, the CAS 10 is also configured to position the robotic guide 50 or guiding surface 54a at a cutting plane which is slightly adjusted/spaced apart from a standard resection. For example, the anterior bone resection can be slightly angled (as referred to by reference numeral 15b in FIG. 4) from the standard anterior bone resection 13b. Similarly, the posterior bone resection can be slightly angled (see reference numeral 16b in FIG. 4) from the standard posterior resection 14b. The angles of the adjusted resections are preferably predetermined so that there is a predetermined distance or offset e.g., at the proximal portion of the end of the cut, i.e., 'X' mm for the anterior cut and/or 'Y' mm for the posterior cut, as indicated in FIG. 4. 'X' and 'Y' are preferably predetermined to correspond to a preferred amount of press-fit interference, for example in the range of 0.05-2 mm, such as about 0.25, 0.5, 0.75, 1.0, 1.25, 1.5, 1.75, and 2.0 mm. This results in additional bone remaining under the femoral implant bone interface surface when the femoral implant is inserted into position, achieving a desired press-fit interference and stressing the bone that is in contact with the implant to a desired degree.

In sum, the computer 100 has stored in memory a plurality of predetermined cut configurations. The plurality of predetermined cut configurations is specific to a particular type and size of implant. The computer 100 is configured to position the guiding surface 54a of the robotic guide 50 or the robotic guide 50 to one of a plurality of predetermined cut configurations relative to the bone interface surface of the femoral prosthesis 2. Typically the bone interface surfaces are planar surface, but can be non-planar surfaces as well. The predetermined cut configurations are preferably a plurality of predetermined planes parallel to or at an angle relative to the bone interface surface of a prosthesis. In other words, the predetermined cut configurations are relative to a bone interface surface of a prosthesis that remains fixed in position at its optimum position on the bone. Thus, the overall position of the prosthesis from its optimum position does not move when repositioning the robotic guide 50 from one predetermined cut configuration to another. The plurality of predetermined planes parallel to the bone interface plane are preferably co-planar to the bone interface plane to provide a congruency fit or offset from the bone interface to provide an interference fit.

The computer 100 i.e., a system controller or processor, has a first module configured to allow a surgeon to select from a plurality or multiple cut configurations for any one particular size of implant. The plurality of or different cut configurations corresponds to different/various degrees or levels of press-fit interference of a prosthesis on bone. An example of a set of cut configurations is illustrated in FIG. 6. Here, each of the plurality of predetermined cut configurations correspond to a standard distal cut, anterior chamfer cut, posterior chamfer cut, and an adjusted anterior cut 15, 17, 19 and an adjusted posterior cut 16, 18, 20 of a distal femur for receiving a femoral prosthesis 2. For example, one cut configuration can include adjusted or offset cuts 15 and 16, and standard cuts 10*b*, 11*b* and 12*b*. This cut configuration could be identified as "Press-fit Option B—0.25 mm" (where 0.25 mm denotes the amount of offset at the proximal end of the cut from the standard cut, in millimeters). Another configuration having a greater degree of press-fit interference could include adjusted cuts 17 and 18, and this can be identified as "Press-fit Option C—0.5 mm." Yet another cut configuration having an even greater degree of press-fit interference could include adjusted cuts 19 and 20, "Press-fit Option D—0.5 mm." Alternatively, the adjusted resections may be arranged such that they are parallel to the standard cuts but offset by a given distance. For example, adjusted cutting planes 15, 17 and 19 can be parallel to the anterior resection 13*b* in the sagittal plane, but offset by the various distances such as 0.25 mm, 0.50 mm and 0.75 mm, respectively. The adjusted posterior resections could be parallel to and offset from the standard posterior resection in a similar manner. This would provide a more uniform degree of press fit along the surfaces of the anterior and posterior resections. Other bone cuts could also be adjusted in either their angle or offset (i.e., parallel but separated by a distance), such as the distal cut or anterior chamfer cut or posterior chamfer cut. Any combination of standard and adjusted bone cuts could be envisioned and applicable to the present invention.

In other words, the CAS 10 is configured to store in memory dimensional data of an implant e.g., femoral, tibial and patellar implants for use in a total knee arthroplasty. In addition, the CAS 10 is configured to store in memory various offset settings that correspond to various "Press-fit Options" to be displayed to the user. The user then selects one of the various "Press-fit Options" displayed for positioning the robotic guide 50 to desired locations corresponding to a desired degree of offset or press-fit interference selected/inputted to the CAS 10 by the user. Alternatively, the user could define a custom "Press-fit Option" by entering the desired angular degree of offset(s) or press-fit interference(s) that may not be included amongst the predefined "Press-fit Options." Input to the CAS 10 is preferably accomplished by input selection via a display 30 in communication with the CAS 10.

In sum, the CAS 10 is configured to intra-operatively receive a selection of one of the plurality of predetermined cut configurations that correspond to various degrees of interference fit of a prosthesis on bone and position the cutting guide to a position corresponding to the selected predetermined cut configuration. The CAS 10 can also intra-operatively receive one or more, e.g., a second, selection of one of the plurality of predetermined cut configurations and position the cutting guide to a position corresponding to the second selected predetermined cut configuration. The user can intra-operatively select and input to the CAS 10 one of the plurality of predetermined cut configurations via an input device, such as touch screen, switch or any other input device readily known in the art.

Furthermore, the CAS 10 includes a memory having a plurality of implant models and a set of default user preferences that corresponds to an interference fit of a prosthesis of a bone for resecting the bone based on a selected implant or implant model, as further defined below. The display 30 also provides a displaying means for displaying the plurality of predetermined cut configurations. The computer 100 is further configured to allow a user to intra-operatively select one of the plurality of predetermined cut configurations displayed on the display 30.

The CAS 10 can also include a module configured to allow the user (e.g., a surgeon) to select the desired degree of press-fit interference they prefer to use from a number of possible configurations (options). The ability to select and/or change the degree of press-fit interference can be performed intra-operatively i.e., at different stages of the surgical procedure (i.e., the different stages of the computer assisted surgical protocol). For example, the surgeon may have a personalized profile or default user preferences stored into the system, such that when their profile is loaded their preferred press-fit option is automatically selected, i.e., a set of default user preferences for resecting bone based on a selected implant or implant model. The module preferably offers the ability to change the preselected option at the beginning of the surgery, or at other points thereafter, such as during the planning stages of the implant, or after making one or more of the bone cuts. This can be accomplished by inputting a desired "Press-fit Option" to the CAS 10 via e.g., a display, keyboard, and the like.

The module is also configured to allow a user to go back and change the degree of press-fit interference after the bone cuts are made, and to readjust and recut certain areas of the resected bone. For example, the surgeon might initially choose "Press-fit Option D—0.75 mm." After performing some or all of the resections with this option, the surgeon may decide to intra-operatively evaluate a quality of the bone or the fit of the implant on the resected bone, e.g., by using a trial component prosthesis. In doing so, he may find that the fit is too tight and the component is too difficult to impact on the bone. That is, he can determine if a repositioning of the cutting guide from the default user preference is required. Therefore, he may decide to change the degree of press-fit interference by selecting Press-fit Option C or B, or the standard cut option A (i.e., no press-fit), and then go back and recut the femur. In this case the robotic guide 50 would be repositioned or the cutting guide surface repositioned at the cut location corresponding to the newly selected press-fit option i.e., one of the plurality of predetermined positions corresponding to varying degrees of interference fit between the implant model and bone model. The surgeon could then recut and remove additional bone, thereby decreasing the tightness/degree of the press-fit interference.

In other words, after a bone resection is made, the user can input into the CAS 10 another desired degree of bone resection based upon an evaluation of the quality of the resected bone or the assessed press-fit interference between the implant and resected bone. That is, the surgeon selects another degree of interference fit between the implant model and the bone model based on the intra-operative evaluation of the resected bone. Upon receipt of the input from the user, the CAS 10 repositions the robotic guide 50 to a subsequent position corresponding to the inputted desired degree of bone resection based upon the assessed press-fit interference. That is, the computer 100 is configured to allow a user to align the guiding surface 54a of the robotic guide 50 i.e., cutting guide, to another one of the plurality of predetermined cut configurations after a cut, such as a first cut, of the bone is completed.

The CAS 10 also permits the surgeon to directly assess the quality of the patient's bone before deciding the degree of press-fit interference to apply, or whether to apply any at all, and to use the bone quality information/data in making his selection for the degree of press-fit interference to apply. The surgeon can assess bone quality intra-operatively at any stage during the procedure. For example, the surgeon can evaluate the bone quality after one or more cuts have been made. While making the cut, the surgeon can feel the progression of the saw-bade through the bone as he is pushing on the saw in order to get a feel for how hard or soft the bone is. He may also evaluate the exposed cancellous bone on the cut surface, using visual and tactile senses (such as a figure tip) to gauge the strength and porosity of the cancellous bone. Alternatively, the surgeon may use an instrument to assess the quality of the bone. The tool could be a simple tool such as an awl or drill that is used to indent or puncture the bone or a hardness testing/indentation tool that may provide a quantitative assessment of the bone properties. Other examples of systems that can be used to assess the quality of cartilage and bone are described in detail in U.S. Patent Application Publication No. 2010/0256504, the entire disclosure of which is hereby incorporated by reference herein.

In other words, the surgeon assesses the desired degree of bone resection for the particular patient based upon bone quality data or assessment of bone quality of the patient. Based upon the bone quality data, the surgeon inputs into the CAS 10 the desired Press-fit Option to apply to the patient, i.e., the user intra-operatively selects another degree of interference fit between the implant model and the bone model based on the intra-operative evaluation of the resected bone.

The CAS 10 can also include an intraoperative imaging modality or sensor to sense the bone quality in the operating room. The intraoperative imaging modality or sensor may provide an objective reading of the bone quality to the surgeon. Such a sensor could be configured to be in communication with the CAS 10 and emit and receive ultrasonic, infrared, ionizing radiation, or other waveforms known to be used for sensing bone quality or density. Such sensors are known in the art and a detailed description of their structure, function and operation is not necessary for a complete understanding of the present invention.

Alternatively, preoperative imaging modalities may be used to assess the bone quality or density of bone, such as radiographs (x-rays), dexa scans, X-ray computed tomography (CT) scans, and magnetic resonance imaging (MRI). Any imaging modality may be used or multiple modalities may be combined, including pre-operative imaging and intra-operative sensing.

The surgeon may choose to take into account any one or a variety of patient factors when making a choice of which level of press-fit interference to use and input to the CAS 10 on the particular patient they are operating on. These may include, but are not limited to: the quality of bone (e.g., hardness, brittleness, density, color, etc.); the morphology of bone and amount of implant-bone coverage (area and shape of cut-surfaces in contact with bone); type of disease (osteoporosis, arthrosis, rheumatoid arthritis, osteo-arthritis, post-traumatic OA, etc.); age; gender; Body Mass Index (BMI); patient history; activity level; susceptibility to pain or degree of pre-operative pain; and bone quality indicators from pre-op imaging: dexa scan, CT grey-level, Hounsfield units (HU), PET, MRI, etc.

In another aspect, the present invention provides a CAS 10 having an implant planning module configured to allow a surgeon to visualize the placement of an implant component on the resected bone surface e.g., via models on a display. Implant placement planning can be performed based on pre-operative imaged-based models, but is preferably performed via intra-operative imageless generic models that are registered to the patient using non-linear morphing techniques. Details regarding image-free registration and bone morphing techniques are disclosed in detail in U.S. Pat. No. 8,126,533, the entire disclosure of which is hereby incorporated by reference herein.

Figure 7:
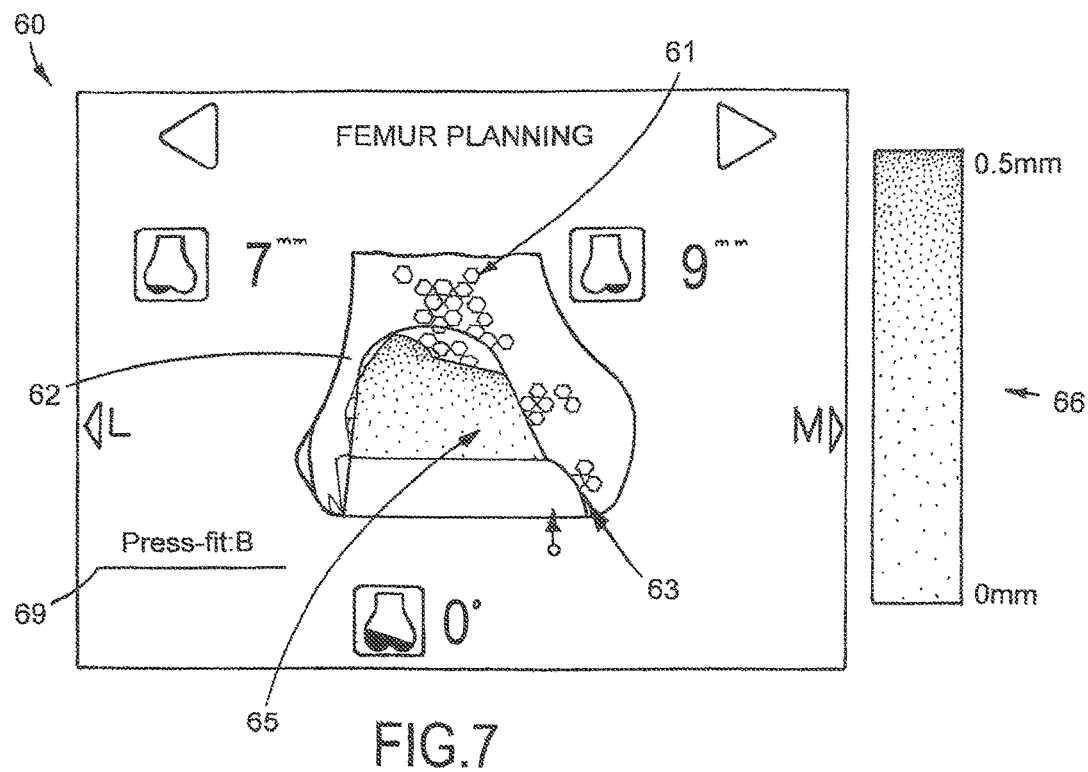
FIG. 7 is a screen shot view of an implant planning screen on a display of the computer assisted surgical system of FIG. 1.

Referring now to FIG. 7, a portion of a femoral implant planning screen 60 of the CAS 10 is shown. The femoral implant planning screen 60 can be shown on a display 30 (FIG. 1) of the CAS 10. The implant planning screen 60 contains one or more views of a bone model e.g., an anterior view of a distal femur bone model 61, as well as the planned implant placement for a given size and position of an implant model e.g., a femoral implant component model 62 on the bone model 61. The planning view also shows the contours of the resected bone model 63 and the contours or perimeter of the implant model 62. The bone-cut contours can change based on the patients' native morphology and the planned position of the femoral implant model 62. Thus, by evaluating the bone-cut and implant contours the surgeon can assess the amount of bone coverage between the implant and bone-cut surface and incorporate this information in choosing how much press-fit interference to apply between the implant and patient's resected bone.

In other words, the surgeon/user can assess the data displayed by the CAS 10 regarding the planned placement of an implant model to a bone model. Then, based upon the surgeon's assessment of the planned placement data, the surgeon can then input to the CAS 10 a desired press-fit interference setting for press-fitting the implant to a patient's resected bone.

The CAS 10 is also configured to display on the display 30 a representation of a degree of interference between the implant model and bone model. The representation is preferably a color map where various colors of the color map are representative of varying degrees of interference. Referring to FIG. 7, the color map 65 on the implant planning screen 60 is indicative of a degree/level or intensity (i.e., deformation or strain) of press-fit interference between the bone model and the implant model based on the selected level of press-fit interference. The color map 65 can be based on the amount of offset between the standard cut and the press-fit cut for a particular implant, and it can be superimposed directly over the modeled bone cut-surfaces 63 and updated in real-time when a new level of press-fit interference is selected (for example, by pressing a button 69 on the touch screen to cycle through the different press fit configurations). A legend or key 66 may also be included to indicate to the surgeon which colors correspond to the various levels of press-fit interference or predicted strain (i.e., grey=0 mm, pink=0.25 mm, red=0.5 mm, blue=0.75 mm, and so on). The surgeon can then use the contact surface area between the bone and implant to decide how much press-fit interference should be applied (for example if the surface of the anterior cut is small and narrow due to the natural morphology of the distal femur, the surgeon may choose to apply more press fit interference to compensate for the smaller amount of coverage). Conversely, if there is a relatively large amount of bone coverage he may choose a smaller amount of press-fit interference in order to prevent the implant from fitting too tightly or to prevent problems due to insertion of the implant.

The CAS 10 can also include a stress modeling or finite element analysis modeling (FE or FEA) module configured to model and evaluate a degree of the press-fit interference of a given implant model and bone model. The FEA model can be patient specific (i.e., derived from pre-operative imaging, such as CT or dexa, or intra-operative imaging) or generic (morphed, from a single generic FE model or database of models) and include measured or inferred values for the mechanical properties of the bone. Bone quality indicators obtained from the intra-operative sensor can also be incorporated in the model. The stress distribution at the bone implant interface can then be modeled as a function of the mechanical bone properties and the level of press-fit interference selected. The stress distribution can also be displayed directly in real time on the planning screen 60 in the form of a color map 65, as discussed above and shown in FIG. 7, with the legend values given in MPa or other appropriate units. Thus, the stress model and implant planning screen 60 can be used to help the surgeon visualize the tightness or degree of the fit and to select the optimal degree of press-fit interference for a particular patient, i.e., be patient specific.

The CAS 10 is also configured to navigate an implant impactor (not shown) i.e., a tool used to impact an implant onto a resected bone), and to determine a final position of the implant relative to a planned or measured bone cuts. The implant impactor can be integrated into and controlled by the CAS 10 e.g., similar to 3D positioning elements of the CAS 10 navigation system.

The CAS 10 can also be configured for use with custom designed prostheses which are custom designed and manufactured for each individual patient (such as those marketed by ConforMIS Inc. of Burlington, Mass.). Such custom implants can be designed based on pre-operative images and generated models of the patient's bones. The amount of press-fit interference can also be custom designed into the prosthesis based on all the above mentioned parameters, including an assessment of the patient's bone quality.

Figure 8:
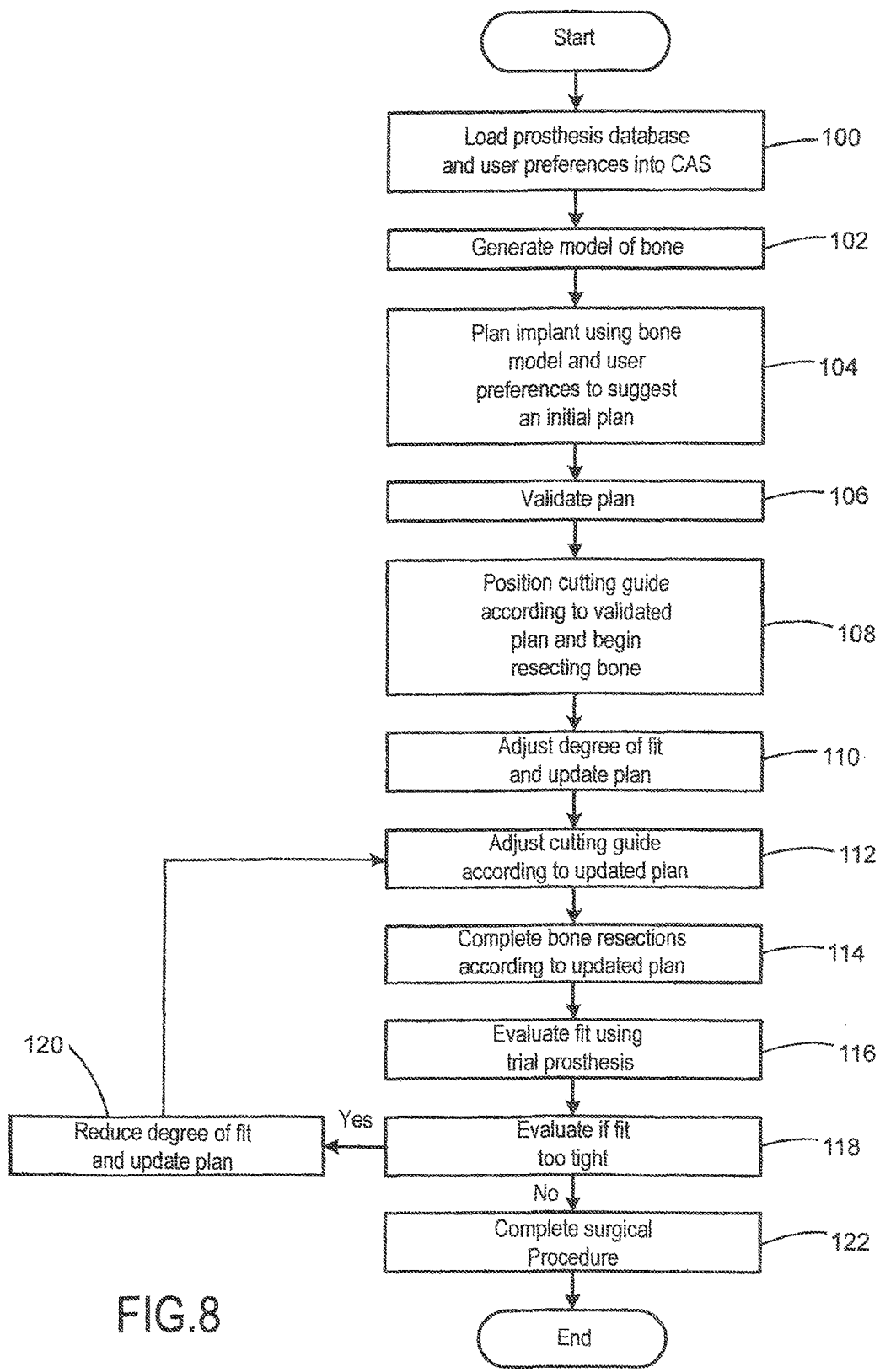
FIG. 8 is a flow chart of a method of preparing a bone in accordance with another preferred embodiment of the present invention.

Referring now to FIG. 8, a flowchart representing an example of a method for preparing a bone for an implant during an arthroplasty in accordance with the present invention is shown. The method includes inputting and loading surgeon preferences regarding desired degrees of press-fit interference for a given type of implant (e.g., TKA implant) into the CAS 10 (step 100) along with data on various implant models having a bone interface. A bone model is then generated by the CAS 10 or the patient's bone anatomy is registered, to which an implant is to be implanted (step 102). The CAS 10 then plans or determines an optimum size and location of the implant to be implanted using the generated bone model and implant model along with user preferences as a suggested initial plan for the user (step 104). That is, an optimum position of the implant model on the bone model is determined. Thereafter, the surgeon intra-operatively evaluates and assesses a quality of the bone of the patient to which the implant is to be implanted. Afterwards, the surgeon selects a degree of press-fit/interference fit to be used for a selected implant and validates the plan for size and location as initially determined by the CAS 10 (step 106). In other words, a degree of interference fit between the implant model and the bone model based on the intra-operative evaluation of the quality of the bone is selected. If no further or additional adjustments to the plan are required, the surgeon mounts/positions a robotic guide 50 having a cutting guide surface on the patient's bone to a position corresponding to the planned and selected degree of press-fit/interference (step 108) i.e. based on the determined optimum position.

After the robotic guide 50 has been mounted to the patient's bone the cutting guide surface is positioned to one of the plurality of predetermined cut configurations that corresponds to the selected degree of interference fit. The surgeon then resects one or more portions of the bone in order to conform the bone to receive the selected implant for implantation thereto (e.g., a distal femoral resection.) Then the surgeon evaluates and assesses the quality of the bone, and in particular a quality of the resected bone. Thereafter, the surgeon inputs into the CAS 10 a updated selection for a degree of press-fit interference to be used based on the bone quality evaluation after an initial resection has been performed (step 110) and repositions the robotic guide 50 to a position corresponding to the updated degree of press-fit selected (step 112). In this step, the entire robotic guide 50 can be repositioned or a cutting guide surface 54 of the robotic guide 50 repositioned. Thereafter, the user resects a subsequent portion of the bone (e.g., an anterior, a posterior, and/or a chamfer resection in the case of a TKA) (step 114).

After all the bone cuts have been made, the surgeon can evaluate the fit of the implant on the resected bone and tightness or degree of fit during impaction of the implant or trial implant to the resected bone (step 116). Based on this assessment, the surgeon can adjust the degree of press-fit interference and update the plan if the fit of the trial component is determined to be too tight (step 120). If any adjustments is necessary, the surgeon then proceeds to adjust the cutting guide according to an updated plan (step 112) and recuts the bone to achieve a better fit (step 114). After all adjustments have been made, and the surgeon has determined that no further adjustments are necessary, the surgeon proceeds to impact the implant on the bone and completes the surgical procedure as usual (step 122).

In addition to the above described embodiments and features of the present invention, the CAS 10 can be configured in a number of variations. For example, autonomous or haptic robotic guides a can be used to machine or burr out the bone, such as those systems developed by MAKO Surgical Corp. or the ROBODOC system, previously marketed by Integrated Surgical Systems (ISS) of Fremont, Calif. Further, bone preparation can be performed by any known method, including sawing, milling, or laser/water jet cutting. The CAS 10 can employ any type of tracking (localization) system, including magnetic, infra-red, ultrasonic, or gyro-accelerometer based systems. The CAS 10 can also be applied to resurfacing implants with curved or curvilinear shaped cuts, such as those used in uni-compartmental arthroplasty or total knee resurfacing.

The systems and methods of the present invention can also be applied to any type of implant (partial and total resurfacing, custom implants) and to other joint replacement procedures (knee, hip, ankle, shoulder, elbow, etc.)

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A computer assisted surgical system for bone cutting operations of an arthroplasty surgery comprising:
a cutting guide to be positioned relative to a first bone; and
a computer in communication with the cutting guide and operatively associated with a memory having computer instructions executable by a processor to
display a first bone cut geometry corresponding to a first interference fit of the implant on the first bone and position the cutting guide to the first bone cut geometry; and
receive a selection of a second bone cut geometry corresponding to a second interference fit of the implant on the first bone and position the cutting guide to the second bone cut geometry.

2. The computer assisted surgical system of claim 1, wherein the first bone cut geometry is a default bone cut geometry stored in the memory.

3. The computer assisted surgical system of claim 2, wherein the default bone cut geometry is a customizable bone cut geometry.

4. The computer assisted surgical system of claim 1, wherein the selection of the second bone cut geometry is based on a quality assessment of the first bone after the cutting guide is positioned to the first bone cut geometry.

5. The computer assisted surgical system of claim 4, wherein the selection of the second bone cut geometry is based on a quality assessment of the first bone after the cutting guide is positioned to the first bone cut geometry and the first bone is resected.

6. The computer assisted surgical system of claim 1, further comprising an intraoperative imaging sensor or a hardness tool for assessing a quality of the first bone.

7. The computer assisted surgical system of claim 6, wherein the intraoperative imaging sensor is an ultrasonic sensor, an infrared sensor, or an ionizing radiation sensor.

8. The computer assisted surgical system of claim 1, wherein the computer is configured to include a preoperative imaging modality for assessing a quality of the first bone.

9. The computer assisted surgical system of claim 8, wherein the preoperative imaging modality assesses the quality of the first bone based on radiographs, dexa scans, X-ray computed tomography scans, or magnetic resonance imaging scans.

10. A method of preparing a first bone for an implant during an arthroplasty using a computer assisted surgery system having a memory storing a plurality of user preferences for resecting the first bone, each of the plurality of user preferences corresponding to an interference fit of a prosthesis on the first bone, comprising the steps of:
intra-operatively positioning a cutting guide operatively in communication with the computer assisted surgery system relative to the first bone;
aligning, with the use of the computer assisted surgery system, the cutting guide to correspond to a first selected user preference for resecting the first bone;
intra-operatively assessing a quality of the first bone; and
determining if a repositioning of the cutting guide from the first selected user preference is required.

11. The method of claim 10, further comprising adjusting a continuous parameter of the plurality of user preferences for resecting the first bone to change a degree of interference fit of the prosthesis on the first bone.

12. The method of claim 10, wherein determining if a repositioning of the cutting guide from the first selected user preference is required is based upon the assessment of the quality of the first bone.

13. The method of claim 10, further comprising aligning the cutting guide to correspond to a second user preference for resecting the first bone based upon the assessment of the quality of the first bone.

14. The method of claim 10, wherein the step of intra-operatively assessing the quality of the first bone is based on a quantitative assessment or qualitative assessment of the first bone.

15. The method of claim 10, wherein the step of intra-operatively assessing the quality of the first bone includes visualizing the first bone to conduct a visual assessment or touching the first bone to conduct a tactile assessment.

16. The method of claim 10, wherein the step of intra-operatively assessing the quality of the first bone is conducted using an ultrasonic sensor, an infrared sensor, an ionizing radiation sensor, radiographs, dexa scans, X-ray computed tomography scans, magnetic resonance imaging scans, or a hardness tool.

17. A method of preparing a bone for an implant during an arthroplasty using a computer assisted surgery system having a memory storing computer instructions executable by a processor, comprising the steps of:
selecting, using the computer, a first cut geometry corresponding to a first interference fit of a prosthesis on the bone;
using the computer assisted surgery system, intra-operatively positioning a cutting guide operatively in communication with the computer assisted surgery system to the first cut geometry;
resecting the bone using the cutting guide positioned at the first cut geometry;
assessing a quality of the resected bone; and
inputting into the computer a second cut geometry corresponding to a second interference fit of the prosthesis on the bone.

18. The method of claim 17, wherein inputting into the computer the second predetermined cut geometry corresponding to the second interference fit of the prosthesis on the bone is based upon the assessment of the quality of the resected bone.

19. The method of claim 17, wherein assessing the quality of the resected bone is based on a quantitative assessment or qualitative assessment of the bone.

20. The method of claim 17, wherein the step of assessing the quality of the resected bone includes visualizing the resected bone to conduct a visual assessment or touching the resected bone to conduct a tactile assessment.

21. The method of claim 17, wherein the step of assessing the quality of the resected bone is conducted using an ultrasonic sensor, an infrared sensor, or an ionizing radiation sensor, radiographs, dexa scans, X-ray computed tomography scans, magnetic resonance imaging scans, or a hardness tool.

* * * * *